(12) United States Patent
Truckai (10) Patent No.: US 12,178,504 B2
(45) Date of Patent: Dec. 31, 2024

(54) SURGICAL SYSTEM AND METHOD OF USE

(71) Applicant: Cirrus Technologies KFT, Budapest (HU)

(72) Inventor: Csaba Truckai, Saratoga, CA (US)

(73) Assignee: Hermes Innovations, LLC, San Jose, CA (US)

( * ) Notice: Subject to any disclaimer, the term of this patent is extended or adjusted under 35 U.S.C. 154(b) by 257 days.

(21) Appl. No.: 15/203,685

(22) Filed: Jul. 6, 2016

(65) Prior Publication Data

US 2017/0056055 A1    Mar. 2, 2017

Related U.S. Application Data

(60) Provisional application No. 62/189,008, filed on Jul. 6, 2015.

(51) Int. Cl.
*A61B 18/18*     (2006.01)
*A61B 17/00*     (2006.01)
(Continued)

(52) U.S. Cl.
CPC ........ *A61B 18/18* (2013.01); *A61B 17/32002* (2013.01); *A61B 17/320068* (2013.01); *A61B 17/42* (2013.01); *A61B 18/082* (2013.01); *A61B 18/14* (2013.01); *A61B 90/30* (2016.02); *A61B 2017/00026* (2013.01); *A61B 2017/00039* (2013.01); *A61B 2017/00057* (2013.01); *A61B 2017/00106* (2013.01);
(Continued)

(58) Field of Classification Search
CPC .............. A61B 34/20; A61B 2090/306; A61B 2017/00026; A61B 2017/00039; A61B 2017/00057; A61B 2017/00106; A61B 2017/00119; A61B 2017/00973; A61B 2017/320064; A61B 2017/320076; A61B 2017/4216; A61B 2018/00601; A61B 2018/00636; A61B 2018/00642; A61B 2018/00702; A61B 2018/00875; A61B 2018/00898; A61B 2018/00904; A61B 2018/1807; A61B 2217/005; A61B 2217/007; A61B 17/320068; A61B 17/320016; A61B 17/32002; A61B 17/42; A61B 18/082; A61B 18/14; A61B 18/18; A61B 90/30; A61B 2090/309; A61F 2/0063

See application file for complete search history.

(56) References Cited

U.S. PATENT DOCUMENTS

| 5,868,673 | A  | 2/1999 | Vesely |
| 7,018,391 | B2 | 3/2006 | Spitz et al. |

(Continued)

FOREIGN PATENT DOCUMENTS

| CN | 102149334      | 8/2011 |
| WO | WO 2001/008578 | 2/2001 |

(Continued)

*Primary Examiner* — Alyssa M Alter
*Assistant Examiner* — Jessandra F Hough
(74) *Attorney, Agent, or Firm* — Levine Bagade Han LLP (57) ABSTRACT

Systems and devices for resecting and removing tissue or organs from the interior of a patient's body, in a minimally invasive laparoscopic procedure while preventing any dispersion of potentially malignant tissue during the resection process.

12 Claims, 8 Drawing Sheets

(51) Int. Cl.
  *A61B 17/32*  (2006.01)
  *A61B 17/42*  (2006.01)
  *A61B 18/00*  (2006.01)
  *A61B 18/08*  (2006.01)
  *A61B 18/14*  (2006.01)
  *A61B 90/30*  (2016.01)
  *A61F 2/00*   (2006.01)

(52) U.S. Cl.
  CPC ............. *A61B 2017/00119* (2013.01); *A61B 2017/00973* (2013.01); *A61B 17/320016* (2013.01); *A61B 2017/320064* (2013.01); *A61B 2017/320078* (2017.08); *A61B 2017/320082* (2017.08); *A61B 2017/4216* (2013.01); *A61B 2018/00601* (2013.01); *A61B 2018/00636* (2013.01); *A61B 2018/00642* (2013.01); *A61B 2018/00702* (2013.01); *A61B 2018/00875* (2013.01); *A61B 2018/00898* (2013.01); *A61B 2018/00904* (2013.01); *A61B 2018/1807* (2013.01); *A61B 2090/306* (2016.02); *A61B 2090/309* (2016.02); *A61B 2217/005* (2013.01); *A61B 2217/007* (2013.01); *A61F 2/0063* (2013.01)

(56) References Cited

U.S. PATENT DOCUMENTS

| | | | |
|---|---|---|---|
| 7,172,603 B2 | 2/2007 | Burbank et al. | |
| 8,974,450 B2 * | 3/2015 | Brannan | A61B 18/1815 606/41 |
| 9,044,210 B1 | 6/2015 | Hoyte et al. | |
| 2004/0082850 A1 | 4/2004 | Bonner et al. | |
| 2006/0200123 A1 | 9/2006 | Ryan | |
| 2008/0281309 A1 * | 11/2008 | Dunning | A61B 18/16 606/32 |
| 2010/0081964 A1 * | 4/2010 | Mark | A61B 10/0283 600/566 |
| 2010/0152756 A1 | 6/2010 | Mark | |
| 2012/0123400 A1 | 5/2012 | Francischelli et al. | |
| 2013/0131457 A1 * | 5/2013 | Seckin | A61B 17/4241 600/235 |
| 2013/0172870 A1 * | 7/2013 | Germain | A61B 18/18 606/115 |
| 2014/0031817 A1 | 1/2014 | Totman et al. | |
| 2014/0276839 A1 | 9/2014 | Forman et al. | |
| 2014/0336643 A1 * | 11/2014 | Orczy-Timko | A61B 18/1447 606/45 |
| 2016/0220314 A1 | 8/2016 | Huelman et al. | |
| 2020/0253639 A1 | 8/2020 | Kim et al. | |
| 2023/0077141 A1 | 3/2023 | Scheib et al. | |
| 2024/0016520 A1 | 1/2024 | Truckai et al. | |

FOREIGN PATENT DOCUMENTS

| | | |
|---|---|---|
| WO | WO 2010/039316 | 4/2010 |
| WO | WO 2014/004051 | 1/2014 |
| WO | WO 2014/013491 | 1/2014 |
| WO | WO 2017/007851 | 1/2017 |

* cited by examiner

SURGICAL SYSTEM AND METHOD OF USE

RELATED APPLICATIONS

This application is a non-provisional of U.S. Provisional Patent Application No. 62/189,008, filed on Jul. 6, 2015, the content of which is incorporated herein by reference in its entirety.

FIELD OF THE INVENTION

The present invention relates to systems and devices for resecting and removing tissue or organs from the interior of a patient's body in a minimally invasive laparoscopic procedure while preventing any dispersion of potentially malignant tissue during the resection process.

BACKGROUND

Several surgical procedures require removing a tissue mass or an organ from the body of a patient in an efficient manner preventing dispersion of potentially malignant tissue during the resection process. One such procedure is a hysterectomy, where a woman's uterus is detached and removed from her body. Hysterectomy is typically performed in cases of severe endometriosis, the presence of fibroids, cancer, cervical dysplasia, uterine prolapse, and more. With the advent of minimally invasive surgery such as laparoscopic surgery, large tissue masses such as the uterus are removed through small incisions, decreasing post operative pain and hospitalization time.

Several types of hysterectomy are performed fully or partially laparoscopically, and these include Total Laparoscopic Hysterectomy (TLH), where the uterus and cervix are removed through a few small incisions made in the abdomen; Laparoscopic Supracervical Hysterectomy (LSH) where the uterus is removed, but the cervix is left intact. In both cases, the uterus is removed through one of the small incisions using an instrument called a morcellator. Another approach is a Total Vaginal Hysterectomy (TVH), where the uterus and\or cervix are removed through the vagina.

In laparoscopic hysterectomies, for example, the uterus is removed using instruments inserted through small tubes into the abdomen, resulting in a few small incisions in the abdomen. A laparoscopic approach offers surgeons better visualization of affected structures (e.g. by using an endoscope) than either vaginal or abdominal hysterectomy.

There remains a need to resect and/or remove tissue from the interior of an organ while maintaining a surface of the organ to prevent tissue from being removed from spreading within the body. Such procedures and devices require an ability for the medical practitioner to be aware of the position of the cutting device relative to the surface of the tissue of the organ while the device is within the organ. This would allow the physician to remove a significant portion of the tissue within the organ and remove the organ from the body. Such devices and systems can be used in any part of the body, with a hysterectomy being one example.

SUMMARY

The present disclosure includes systems and methods for resecting and/or removing tissue from the interior of an organ and monitoring a proximity of the tissue removal device to a surface of the organ to prevent the surface of the organ from being cut or breached by the cutting device. In some variations, the cutting device advances through the outer surface of the organ when inserted into a cavity within the organ. In alternate variations, the device is introduced through an opening of the organ. The devices and methods described herein are explained with respect to performing a hysterectomy. However, the methods, devices, and systems can be used in any body location unless otherwise specifically claimed.

In one example, the prevent disclosure teaches a system for resecting tissue within an interior of an organ. Such a variation can include a probe having a proximal portion and a distal portion; a cutting member configured to remove tissue and located at the distal portion of the probe; at least one sensor located adjacent to the cutting member, the sensor configured to generate a signal comprising an environmental condition adjacent to the cutting member; and a controller configured to receive the signal of the environmental signal and use the signal to determine whether the cutting member is adjacent to an exterior surface of the organ.

The sensor can comprise a mechanism selected from a group consisting of: a capacitance sensing mechanism, an impedance sensing mechanism, an optical sensing mechanism, and an ultrasound mechanism.

In one variation of the system, the controller is configured to generate an alert signal upon detecting that the cutting member is adjacent to the exterior surface of the organ. Such an alert signal can comprise an aural alert, a visible alert, a tactile alert, and a combination thereof.

The probe and cutting mechanism can comprise a mechanical or an electrosurgical based cutting mechanism. In certain variations, the sensor is located adjacent to the cutting mechanism or adjacent to a window or opening in the probe that exposes the cutting member.

In variations where the cutting mechanism comprises an electrosurgical cutting mechanism, the cutter can comprise an electrode element, a resistively heated element, an inductively heated element, an ultrasound transmission element, and a light energy transmission element.

The controller of the present system can include an algorithm for de-activating the cutting member in response to the signal that the cutting member is within a predetermined proximity to the organ surface. The algorithm can also modulate the speed that the cutting member removes tissue.

The systems described herein can further comprise a negative pressure source in fluid communication with the probe and cutting mechanism, where the negative pressure source extracts resected tissue through a passageway in the probe. Alternatively or in combination, the systems can comprise a positive pressure source in fluid communication with the probe.

The present disclosure also includes methods for resecting tissue. In one such variation, the method can comprise introducing a probe into an interior of an organ, wherein a working end of the probe includes a cutter and sensor mechanism adjacent to the cutter, where the sensor mechanism is configured to detect a surface of the organ; resecting tissue with the cutter generating a signal with the sensor mechanism when the sensor mechanism detects the cutter approaching the organ surface from the interior of the organ; and removing a substantial volume of the organ from within the interior of the organ without the cutter perforating the organ surface from the interior thereby preventing dispersion of potentially malignant tissue.

The method can further include variations where the sensor mechanism comprises at least one of a capacitance sensing mechanism, an impedance sensing mechanism, an optical sensing mechanism, and an ultrasound mechanism. In an additional variation, the sensor mechanism is operatively coupled to a controller to provide signals consisting of at least one of aural, visible or tactile signal.

The method can also include a controller that employs an algorithm for de-activating the cutter in response to a signal that the cutter is within a pre-determined proximity to the organ surface. The de-activating step can comprise stopping movement of the cutter or stopping energy delivery to the cutter. In additional variations, the controller includes an algorithm for modulating the speed of movement of the cutter in response to the signal that the cutter is within a pre-determined proximity to the organ surface.

Variations of the method can also include mobilizing the organ with the intact organ surface after the substantial volume is removed and removing the organ from the patient's body.

In an additional variation, a method of resecting tissue comprises introducing a probe into an interior of an organ, wherein a probe working end includes a first sensor component; disposing a second sensor component at an exterior surface of the organ; and activating the probe to resect tissue wherein the first and second sensor components cooperate to provide at least one signal indicating a proximity of the probe to the exterior surface of the organ. At least one of the sensor components comprises a component selected from the group consisting of a capacitance sensing mechanism, an impedance sensing mechanism, an optical sensing mechanism, and an ultrasound mechanism and the other sensor component cooperates to enhance a sensitivity of said signals.

The sensor component can include a gas, liquid, or gel disposed at the exterior of the organ. Alternatively, or in combination, the second sensor component comprises a sac disposed at the exterior of the organ.

In an additional variation, the present disclosure includes a method for laparoscopic hysterectomy. For example, the method can include introducing a probe into a uterine cavity, wherein a probe working end includes a sensor mechanism for sensing the proximity of the cutter to an exterior surface of a uterine wall; activating the probe to resect tissue from within the uterine cavity wherein the sensor mechanism provides signals indicating the proximity of the cutter to said exterior surface; and removing a substantial volume of the tissue from within the uterine cavity without perforating the uterine wall thereby preventing dispersion of potentially malignant uterine tissue. The method can also include the step of sealing and/or ligating blood vessels communicating with the uterus.

The method can further comprise removing a substantial volume of the tissue within the uterine cavity without perforating the uterine wall from within the cavity such that the uterine wall forms an intact shell. The method can also include transecting the shell of the uterine wall away from the patient's body.

The methods and/or devices described herein can be performed in a supracervical procedure, a trans-vaginal approach, an endoscopic approach, or in an open surgical approach.

In an additional variation, a method of resecting at least a portion of an organ can include isolating the tissue mass or organ from its blood supply; introducing a resecting probe into the organ, wherein a probe working end includes a cutter and sensor mechanism for sensing the proximity of the cutter to a surface of the organ; activating the cutter to resect tissue wherein the sensor mechanism provides signals indicating the proximity of the cutter to the organ surface; and removing a substantial volume of the organ without perforating the organ surface thereby preventing dispersion of potentially malignant tissue.

BRIEF DESCRIPTION OF THE DRAWINGS

The disclosed variations will next be described in greater detail by reference to exemplary embodiments that are illustrated in the drawings.

DETAILED DESCRIPTION OF THE INVENTION

Figure 1:
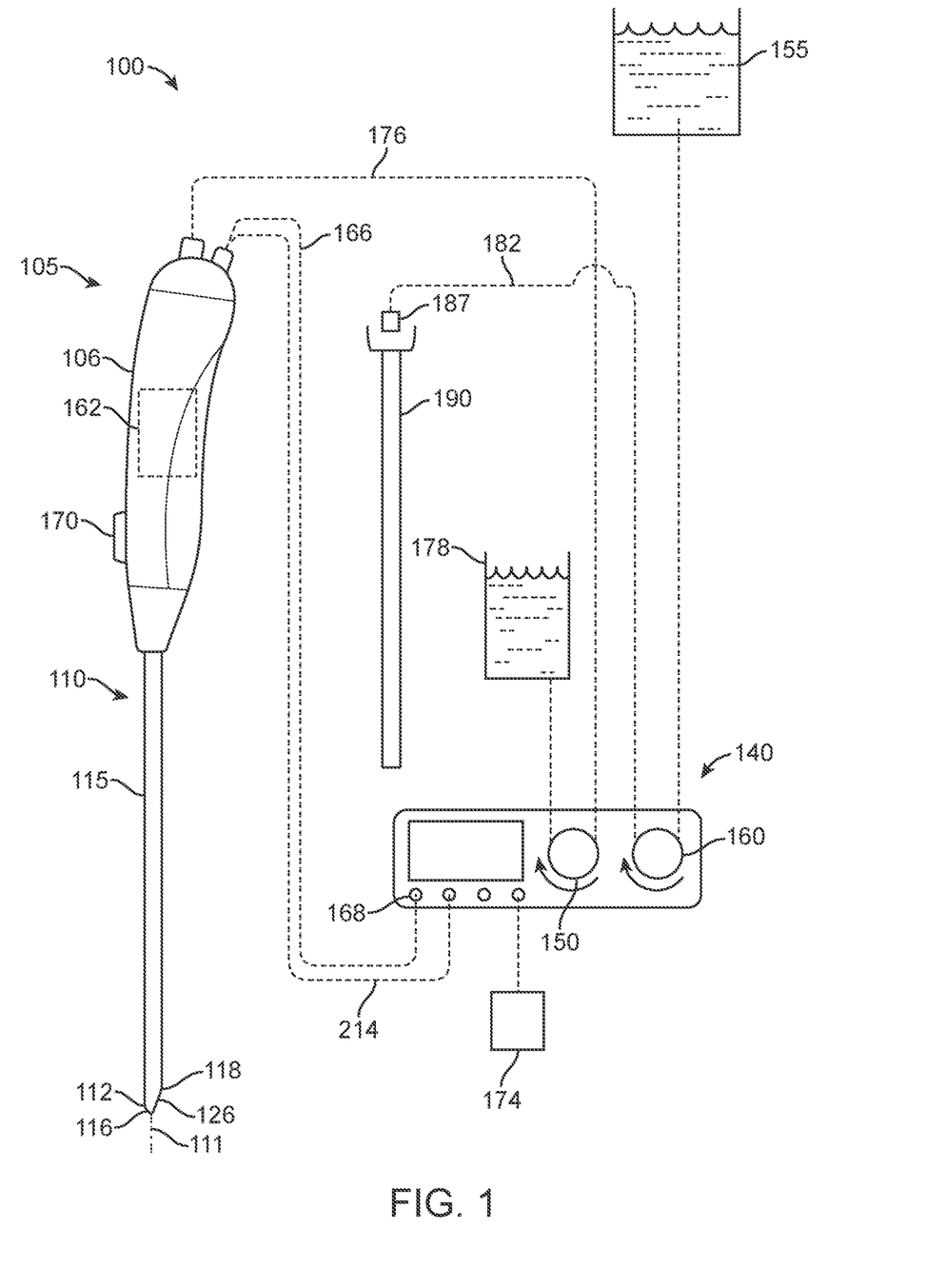
FIG. 1 is a schematic view of a tissue resection device and a block diagram of operating components corresponding to the invention for use in a laparoscopic resection procedure.
Figure 2:
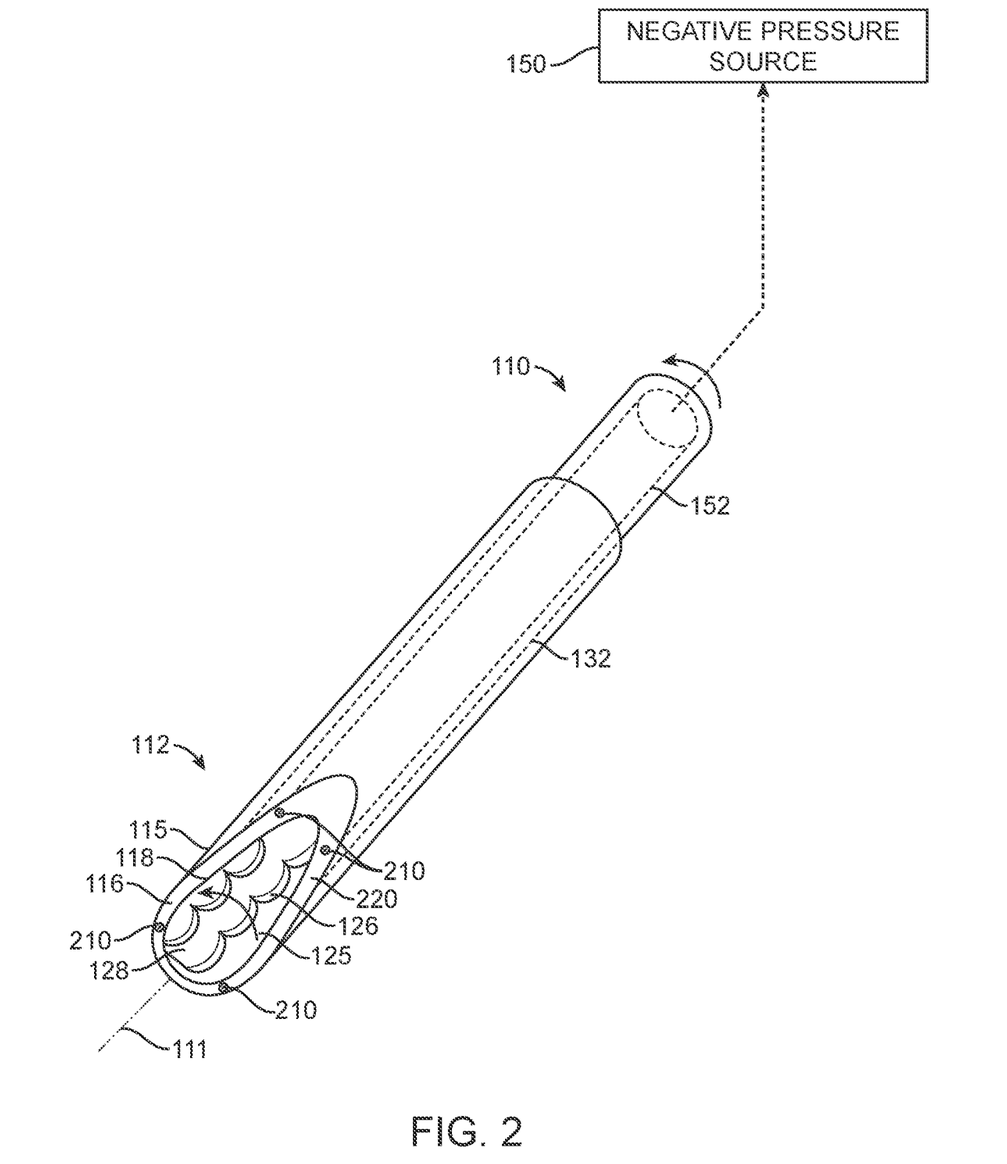
FIG. 2 is a perspective view of the working end of a resection device of the type shown in FIG. 1, showing a sensor mechanism carried by the working end.

FIGS. 1 and 2 illustrate a tissue resection system 100 that includes a hand-held single-use tissue cutting device or resection device 105. The device 105 has a handle portion 106 that is coupled to a shaft portion 110, having an outer diameter ranging from about 3 mm to 20 mm. The shaft portion 110 extends along axis 111 and can have a length suitable for introducing directly into a body space or into an organ, for example, introducing through a trocar in a laparoscopic procedure or for introducing through a working channel of an endoscope.

In one variation, a hand-held resecting device 105 as depicted in FIGS. 1 and 2 can be used to perform a laparoscopic hysterectomy procedure as depicted in FIGS. 3A to 3D. Referring to FIGS. 1 and 2, the resection device 105 is a tubular cutter as is known in the art with a shaft portion 110 and working end 112. The shaft 110 comprises an assembly of a first or outer sleeve 115 extending along axis 111 to a distal end 116, having a window 118 therein for receiving tissue. A second or inner sleeve 125 with a distal blade edge 126 and distal opening 128 is dimensioned to rotate in bore 132 of outer sleeve 115. The outer and inner sleeves, 115 and 125, can be fabricated of thin-wall stainless steel, but any other suitable materials can be used. As can be understood from FIGS. 1-2, rotation of the inner sleeve 125 will cut tissue captured in the window 118 of the outer sleeve. FIG. 2 shows the working end 112 of the assembly of outer sleeve 115 and inner sleeve 125 with the inner sleeve 125 rotating and in a partially window-open position.

As can be seen in FIG. 1-2, the resection system 100 can include a controller 140 that is adapted for (i) controlling a motor drive in the resecting device 105 as will be described below; (ii) controlling at least one sensor system carried by the resection device 105 that will be described further below, (iii) controlling a negative pressure source or outflow pump 150 operatively coupled to a tissue extraction channel 152 in the resection device 105, and (iv) controlling an optional fluid source 155 and inflow pump 160 for distending or flooding a treatment site with a fluid, such as saline.

Referring FIG. 1, the controller 140 includes algorithms for driving a motor 162 in the handle 106 of the resecting device 105. The motor can be a brushless DC motor and controller 140 can be configured to operate the motor at a preset RPM or a user-selected RPM between 100 and 2,000 RPM. FIG. 1 shows an electrical cable 166 extending from connector 168 in the controller 140 to the resecting device handle 106. The resecting device 105 can be operated by a switch 170 in the handle 106 or a footswitch indicated that 174 coupled to the controller 140.

Still referring to FIG. 1, the controller 140 includes a roller pump 150 that provides a negative pressure source for extracting tissue through the passageway 152 in the resecting device 105. The roller pump 150, in combination with the flexible tubing 176, is configured to pump fluid and extracted tissue chips through the tubing into the collection reservoir 178.

Again referring to FIG. 1, controller 140 can have a second roller pump 160 adapted to provide fluid flows into a site targeted for resection. A fluid source 155 is coupled to a flexible fluid infusion tubing 182 that is engaged by the roller pump 160 and that further extends to a fitting 187 on cannula 190, which is adapted for access to the treatment site. The cannula 190 can be inserted into the site and can be used as an access pathway for the resection device 105, or the cannula can be used for fluid infusion independent of the resection device. In another variation, the fluid infusion tubing 182 can be coupled to the resection device 105 so that fluid flows to the working end 112 and window 118 in a path in the annular space between the outer sleeve 115 and the inner sleeve 125.

Now turning to FIG. 2, the working end 112 of the resecting device 105 is shown in an enlarged perspective view. In one variation shown in FIG. 2, a sensor system is shown disposed around the cutting window 118 in the working end. This variation shows four capacitance sensors 210 disposed around the window 118, which comprise the distal termination of paired wire leads as is known in the art capacitance sensors. The capacitance sensors 210 are coupled to the controller 140 through cable 214 (FIG. 1). The sensors 210 can be carried in a thin polymeric coating 220 on the outer sleeve 125. In this embodiment, there are four capacitance sensors, but there could be from 1 to 20 sensors on the outer sleeve 125. In another variation, one or more capacitance sensors could be carried on the inner sleeve surface opposing the sharp blade edges. As will be described below, capacitive sensors 210 can provide a signal to the user when the cutting blade 126 (FIG. 2) approaches the periphery of an organ targeted for resection. While FIG. 2 shows a variation of the resecting device 105 with capacitance sensors 210, it should be appreciated that other types of sensors can be used to determine the proximity of the cutting blade to an organ periphery, such as optical sensors, impedance sensors, magnetic sensors and the like.

Figure 3A:
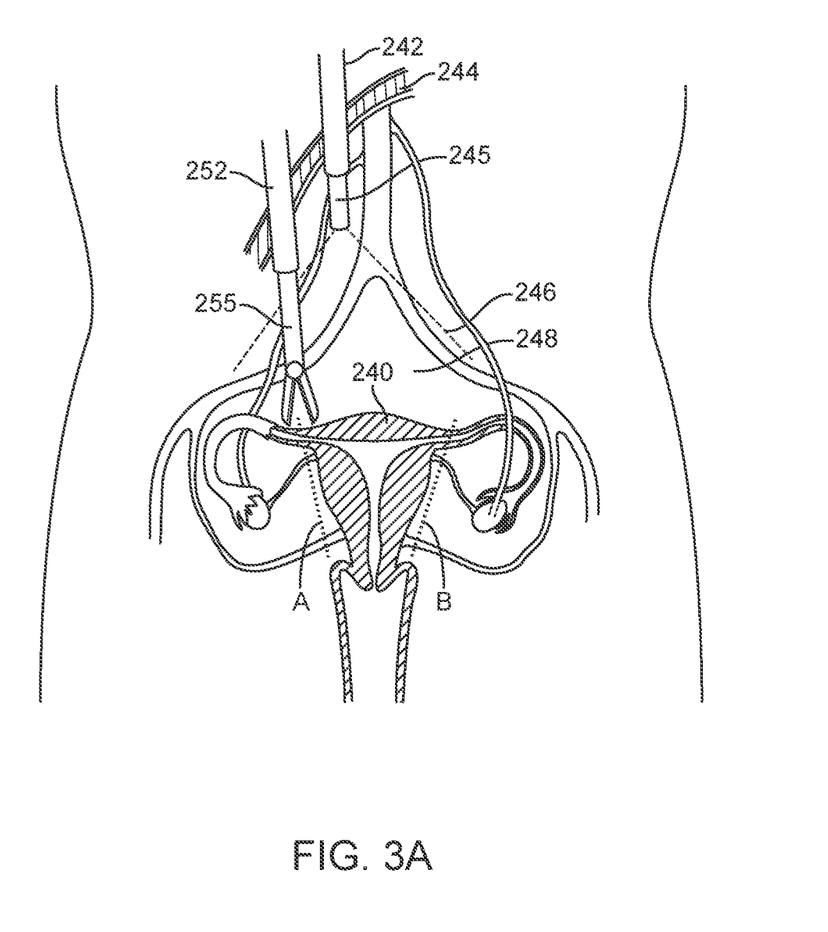
FIG. 3A is a schematic view of the patient's uterus and abdominal region showing the initial steps of a laparoscopic hysterectomy procedure with an ultrasound component de-coupled from a resection device. The ultrasound component can optionally include a plurality of piezoelectric elements carried therein.

Now turning to FIGS. 3A to 3D, a method corresponding to the invention is described relating to the resection of a uterus in a new form of laparoscopic hysterectomy. FIG. 3A is a schematic view of the patient's abdominal cavity and a uterus 240 targeted for resection. In a first step of the method, a first sleeve or cannula 242 is introduced through the abdominal wall 243, and an endoscope 245 is inserted through the sleeve to provide a field of view 246 in the abdominal cavity 248.

FIG. 3A further shows a second cannula 252 introduced through the abdominal wall 243, after which a cutting-sealing device 255, such as electrosurgical cutting and sealing device, is introduced through the cannula 252 for use in sealing and transecting blood vessels communicating with the uterus 240. As is known in the art of performing a laparoscopic hysterectomy, the uterine arteries are sealed and transected, and the broad ligaments, fallopian tubes, and fascia are transected along lines A and B to mobilize the uterus 240. Thereafter, the cutting-sealing device 255 is withdrawn from cannula 252.

Figure 3B:
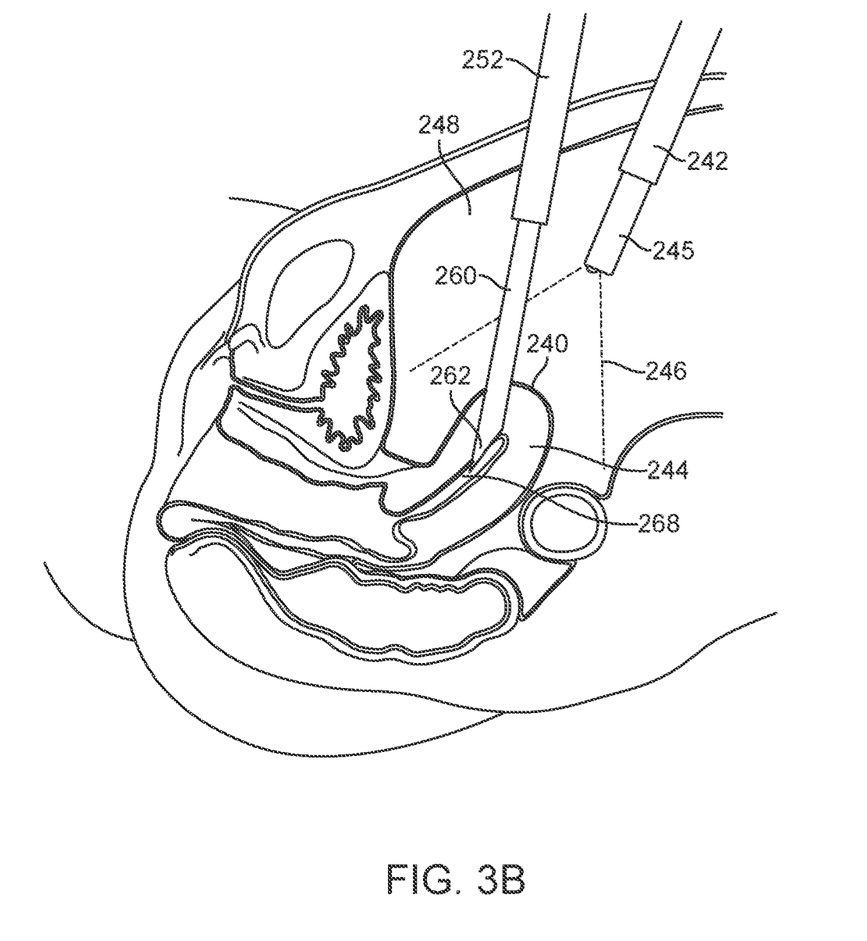
FIG. 3B is a sagittal view of the patient's uterus and abdominal cavity, showing another step comprising introducing a trocar through the uterine wall from the abdominal cavity.

FIG. 3B depicts a subsequent step of the method wherein a sharp trocar sleeve 260 is introduced through the second cannula 252 by the physician, and then, under laparoscopic vision, the distal tip 262 of the trocar sleeve 260 is advanced through the uterine wall 244 into the uterine cavity 268.

Figure 3C:
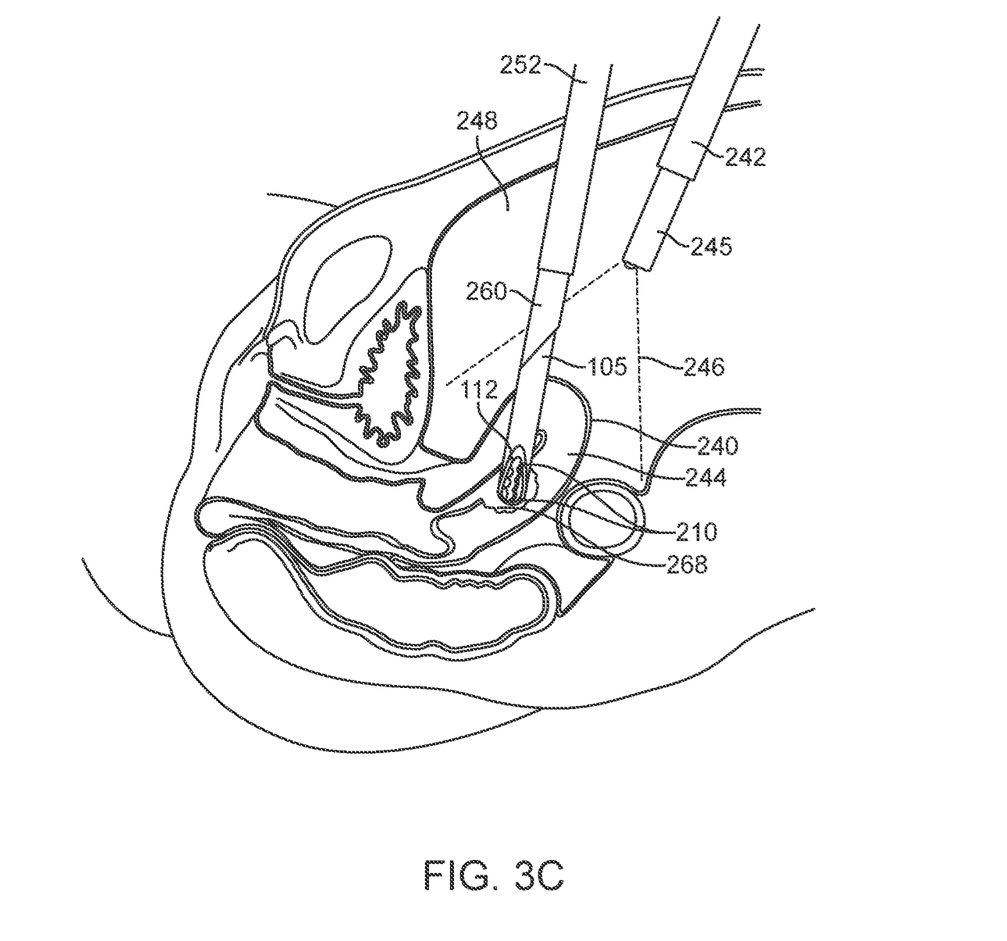
FIG. 3C is a sagittal view of a step comprising introducing the resecting device into the interior of the uterus, actuating the device to reset tissue, and removing tissue through the passageway in the resecting device.

FIG. 3C shows the next step in the method wherein the resection device 105 is introduced through the cannula 252 and trocar sleeve 260 into the interior of the uterus 240, and thereafter the trocar sleeve 260 is withdrawn, leaving the working end 112 of the resection device 105 within the interior of uterus 240. In one variation of the method, the fluid source 155 and infusion tubing 182 are coupled to the resection device 105 to provide a fluid flow into the uterine cavity 268 through the annular space between the outer sleeve 115 and the inner sleeve 125 (see FIGS. 1-2). By this means, the uterine cavity 268 can be distended to some extent, while the controlled fluid inflow assists in the resecting procedure and further assists in the extraction of tissue debris from the site. In another variation (not shown), a cervical seal member can be introduced trans-vaginally to seal the uterine cavity 268, wherein the cervical seal can be a probe shaft, an inflatable member, or other types of seals known in the art. In another variation, the fluid source 155 and infusion tubing 182 can be coupled to a trans-cervical probe and seal (not shown) to provide a fluid flow into the uterine cavity 268.

Figure 3D:
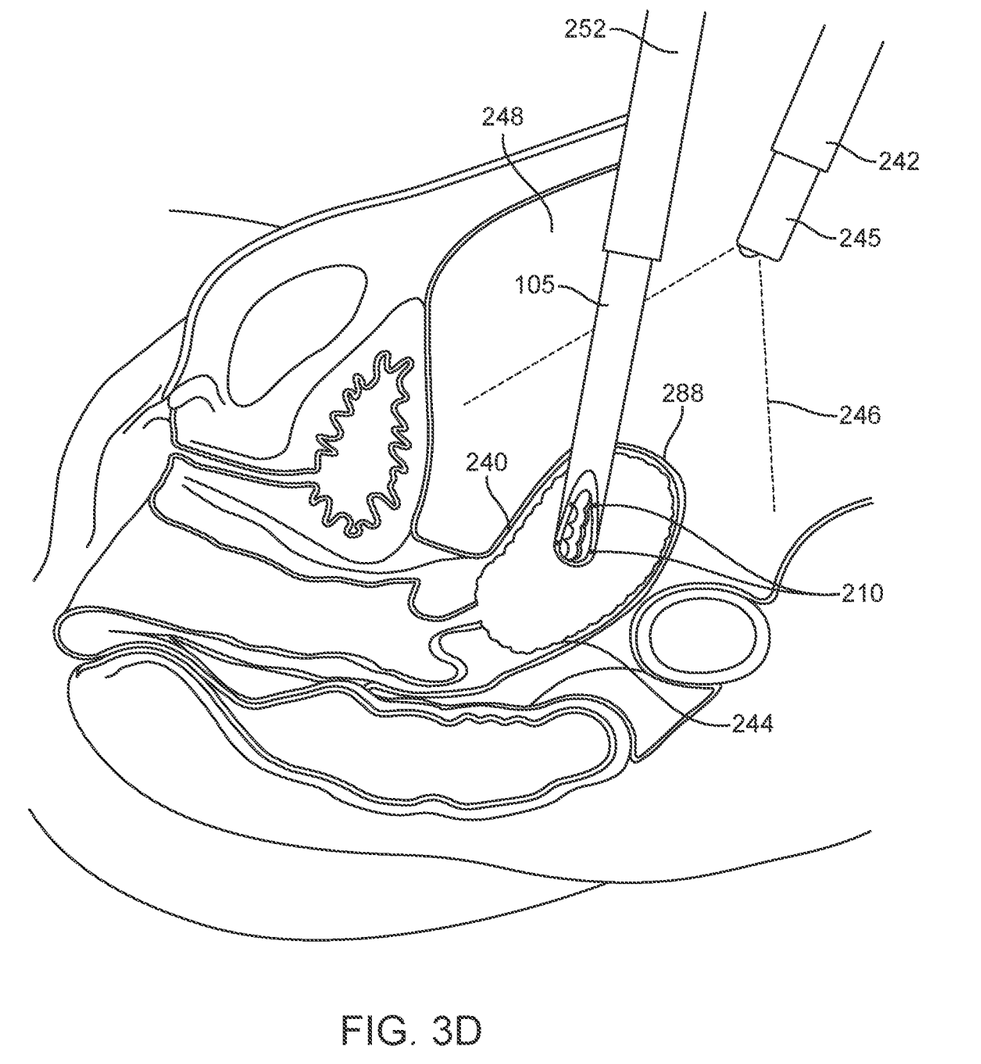
FIG. 3D is a sagittal view of a further step comprising introducing utilizing the resecting device to reset and remove a substantial volume of the interior of the uterus while sensor mechanisms indicate and/or control when a cutting member comes into proximity to the wall of the uterus.

Still referring to FIG. 3C, the physician then can actuate the resecting device 105 to resect tissue in a blind method while observing the exterior of the uterus 240 with the endoscope 245. The physician can manipulate the working end 112 of the resecting device 105 to core out the interior of the uterus 240 while leaving the uterine wall 244 completely intact as it cores tissue from within and apart from any access openings. It can now be seen that the purpose of the capacitance sensors 210 is to provide signals to indicate the proximity of the cutting blade 126 to the exterior of the uterine wall 244. As indicated in FIG. 3D, in one variation, the capacitance sensors 210 can sense a change in tissue capacitance when the window 118 and blade move close to the exterior of the uterine wall 244. The plurality of capacitive sensors 210, as shown in FIG. 2, allows for sensing proximity to the surface of the uterine wall no matter the orientation of the working end 112. The resecting procedure can be considered complete when the physician has removed a substantial volume of tissue from the interior of the uterus 240 and, in effect, leaves only a shell 288 of the uterus in place, as shown in FIG. 3D. By this means, it can be understood that no resected tissue, and thus no potentially malignant tissue, has been exposed outside of the interior of uterus 240. Rather, all tissue has been resected and immediately extracted through passageway 152 in the inner sleeve 125 and then collected in the collection chamber 178 with no possibility of contaminating the abdominal cavity 248. In one aspect of the method, at least 50%, at least 60%, at least 70%, at least 80%, or at least 90% of the mass of the uterus 240 is resected and extracted to leave a reduced-volume shell 288 of the uterus (FIG. 3D). Following the resection and extraction of the bulk of the uterus 240, the reduced-volume shell 288 of the uterus can be removed in methods known as in a conventional supracervical or other laparoscopic hysterectomy procedure. Typically, the reduced-volume uterine shell 288 can be removed intact in a transvaginal approach.

During the resection steps described above, the controller 140 can modulate fluid inflows to and from the site by controlling the roller pumps. The flow rates into and out of the uterine cavity 268 can be from 10 mL/min to 1000 mL/min and also can be modulated depending on a cutting speed selected by the physician.

Figure 4:
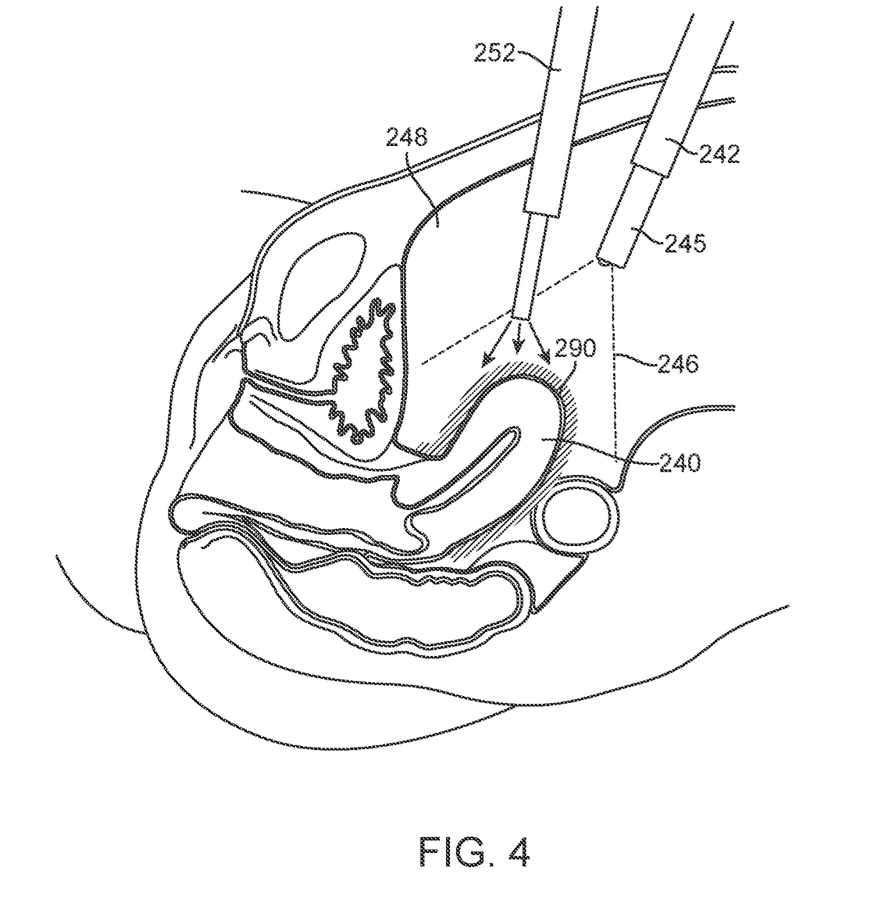
FIG. 4 is a sagittal view of the patient's uterus, and abdominal cavity showing the variation in the method wherein a sensor responsive media is applied around the exterior surface of the uterus.
Figure 5:
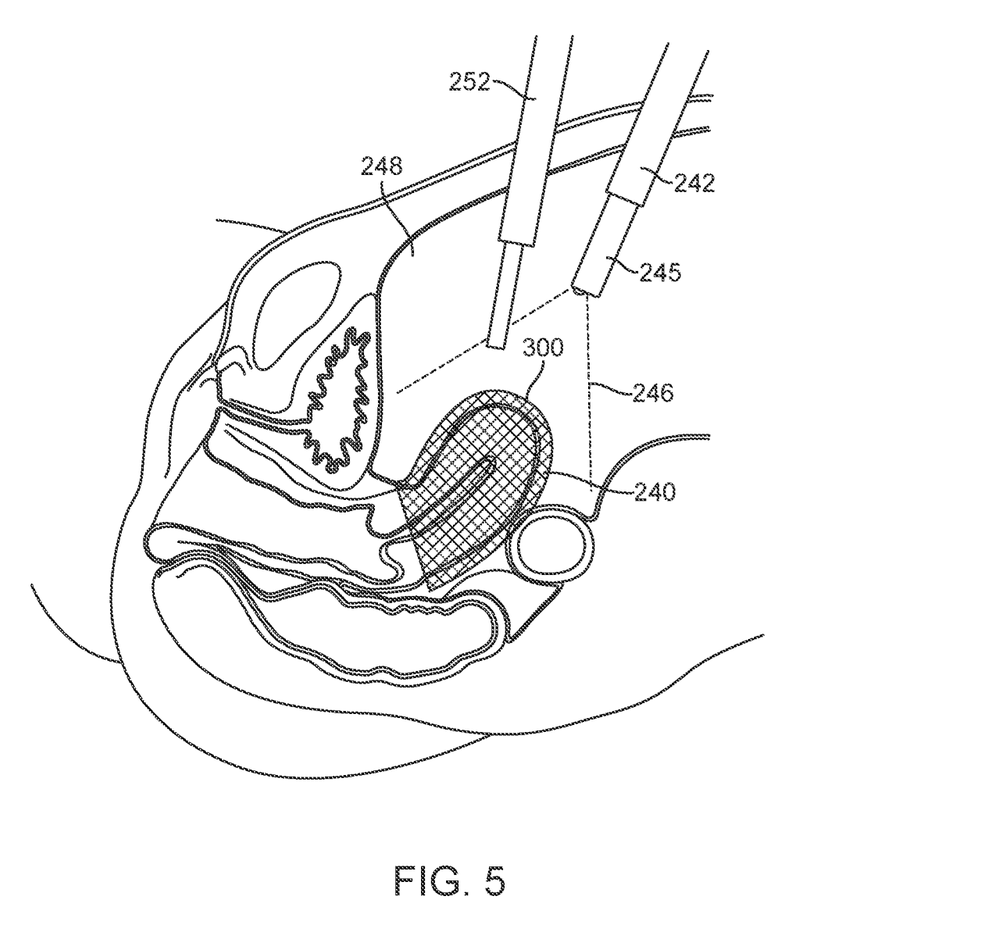
FIG. 5 is another sagittal view of the patient's uterus and abdominal cavity, showing another variation in the method wherein a sensor responsive mesh sac is disposed around the exterior surface of the uterus.

In another embodiment in another variation shown in FIG. 4, a sensor enhancing media may be sprayed, painted, flooded, or otherwise disposed around the exterior of uterus 240 to enhance the sensitivity of the capacitance sensors 210 or other sensing mechanism. For example, FIG. 4 illustrates a conductive gel 290 that may be sprayed or painted onto the exterior of the mobilized uterus 240, which will increase the resolution of the capacitive sensors 210. Such a media 290 can be a conductive gel, such as a hypertonic saline gel. A similar conductive gel would enhance the resolution impedance sensors. In another variation, a magnetic sensitive material could be disposed around the uterus 240, which could increase the resolution of a magnetic sensor carried by the working end 112 of the resecting device 105. In another variation shown in FIG. 5, a mesh net 300 can be disposed around the uterus 240 for similar purposes. For example, a structure similar to that stretchable nylon stocking with conductive threads could be disposed around the uterus 240 to increase the sensitivity of a capacitance sensor 210, an impedance sensor, or a magnetic sensor.

In another variation, a source of illumination or light emitters may be disposed in one or more locations around the window 118 of the exterior sleeve 125. Such illumination or light emitters can be added to the device of FIG. 2 or can be used instead of capacitance sensors 210 or other sensors. The light emitters can be, for example, a distal end of one or more optical fibers, an LED source, or other source of visible illumination. It can be understood that the physician then can see the brightness of the light through the translucent uterine wall and understand the proximity of the cutting blade 126 to the wall surface.

In one variation, the controller 140 includes algorithms to modulate or terminate operation of the resecting device 105 when the capacitance sensors 126 or other sensor mechanism indicate the proximity of the cutting blade to the exterior of uterine wall 244. In another variation, the sensor system can provide warning signals to the position of the cutting blade in the form of aural, visual or tactile signals.

By using the system and method described above, it can be understood that the laparoscopic hysterectomy can be performed without risk of dispersing any potentially malignant tissue in the abdominal cavity 248. All resected tissue chips are maintained within the interior of the uterus 240 with the uterine wall itself functioning as a containment sac. The system and method can be performed with any type of resecting device, such as a mechanical cutter as shown herein, in which a blade can cut by rotation, reciprocation or both. In other variations, the resecting device may be an RF device, ultrasound device, laser device, microwave device, resistive heat device or the like.

What is claimed is:

1. A method of resecting tissue, comprising:
positioning a stretchable structure having a thin wall around an exterior of a uterus, where the stretchable structure comprises an electrically conductive material that enhances a sensitivity of a sensor system;
introducing a probe into an interior of the uterus, the probe having an inner sleeve and an outer sleeve, wherein a working end of the probe includes a motor-driven cutter on the inner sleeve exposed at a window of the outer sleeve, wherein the working end carries an electrical component of the sensor system that is configured to detect the electrically conductive material of the stretchable structure such that the sensor system detects the motor-driven cutter approaching a surface of the uterus;
activating the motor-driven cutter to resect uterine tissue at the window with the motor-driven cutter;
providing an electrical current to the electrical component and using a controller to monitor impedance between the electrical component and the electrically conductive material of the stretchable structure, wherein the controller is configured to detect that the electrical component on the working end of the motor-driven cutter is approaching the electrically conductive material of the stretchable structure from the interior of the uterus;
and removing a substantial volume of the uterus from within the interior of the uterus without the motor-driven cutter perforating the surface of the uterus to prevent dispersion of potentially malignant tissue outside of the uterus.

2. The method of claim 1 wherein the sensor system comprises at least one of a capacitance sensing mechanism, an impedance sensing mechanism, an optical sensing mechanism and an ultrasound mechanism.

3. The method of claim 1 wherein the motor-driven cutter includes a moveable blade edge configured for resecting tissue.

4. The method of claim 1 wherein the motor-driven cutter includes an energy transmission element configured for resecting tissue.

5. The method of claim 4 wherein the energy transmission element comprises at least one of an electrode element, a resistively heated element, an inductively heated element, an ultrasound transmission element and a light energy transmission element.

6. The method of claim 1, wherein the controller generates a signal when the moto-driven cutter approaches the stretchable and the signal consist of at least one of aural, visible or tactile signals.

7. The method of claim 6 wherein the controller includes an algorithm for de-activating de-activates the motor-driven cutter when the sensor system mechanism detects that the motor-driven cutter is within a pre-determined proximity to the surface of the uterus or the stretchable structure.

8. The method of claim 7 wherein de-activating the motor-driven cutter comprises at least one of stopping movement of the motor-driven cutter or stopping energy delivery to the motor-driven cutter.

9. The method of claim 6 wherein the controller includes an algorithm for modulating a speed of movement of the motor-driven cutter in response to the signal that the motor-driven cutter is within a pre-determined proximity to the surface of the uterus or the stretchable structure organ.

10. The method of claim 6 wherein the controller includes an algorithm for modulating energy delivery to the motor-driven cutter in response to the signal that the motor-driven cutter is within a pre-determined proximity to the surface of the uterus.

11. The method of claim 1 wherein the motor-driven cutter is moveable relative to the window by at least one of rotation and reciprocation.

12. The method of claim 1 further comprising applying a negative pressure source to extract resected tissue from the working end through a passageway in the probe.

* * * * *